(12) United States Patent
Toyohara et al.

(10) Patent No.: US 9,314,046 B2
(45) Date of Patent: *Apr. 19, 2016

(54) FLAVOR-IMPROVING METHOD

(75) Inventors: Yoshikazu Toyohara, Tokyo (JP);
Tadahiro Hiramoto, Yokohama (JP);
Naoto Omotani, Kamakura (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 62 days.

This patent is subject to a terminal disclaimer.

(21) Appl. No.: 14/232,316

(22) PCT Filed: Jul. 12, 2012

(86) PCT No.: PCT/JP2012/067781
§ 371 (c)(1),
(2), (4) Date: Jan. 13, 2014

(87) PCT Pub. No.: WO2013/008875
PCT Pub. Date: Jan. 17, 2013

(65) Prior Publication Data
US 2014/0170082 A1 Jun. 19, 2014

(30) Foreign Application Priority Data
Jul. 14, 2011 (JP) ................................. 2011-155323

(51) Int. Cl.
*A61K 47/22* (2006.01)
*A61K 8/49* (2006.01)
*A61K 8/44* (2006.01)
*A61K 47/18* (2006.01)
*A61Q 11/00* (2006.01)
*A23L 1/227* (2006.01)
*A23L 1/226* (2006.01)
*A23G 3/36* (2006.01)
*A23L 2/56* (2006.01)
*A23L 1/22* (2006.01)

(52) U.S. Cl.
CPC .............. *A23L 1/22671* (2013.01); *A23G 3/36* (2013.01); *A23L 1/227* (2013.01); *A23L 1/22075* (2013.01); *A23L 1/22083* (2013.01); *A23L 1/22091* (2013.01); *A23L 2/56* (2013.01); *A61K 8/44* (2013.01); *A61K 8/498* (2013.01); *A61K 47/183* (2013.01); *A61K 47/22* (2013.01); *A61Q 11/00* (2013.01)

(58) Field of Classification Search
None
See application file for complete search history.

(56) References Cited

U.S. PATENT DOCUMENTS

| 6,890,574 | B1 | 5/2005 | Geifman et al. | |
| 2002/0188019 | A1* | 12/2002 | Ley et al. | 514/456 |
| 2008/0057174 | A1 | 3/2008 | Yamakoshi et al. | |
| 2009/0004332 | A1 | 1/2009 | Katzir et al. | |
| 2009/0155420 | A1 | 6/2009 | Zhang et al. | |
| 2010/0151055 | A1* | 6/2010 | Riess et al. | 424/679 |
| 2010/0331349 | A1* | 12/2010 | Ley et al. | 514/263.34 |

FOREIGN PATENT DOCUMENTS

| CN | 1937929 | A | 3/2007 |
| EP | 1258200 | A2 | 11/2002 |
| JP | 2002-360188 | A | 12/2002 |
| JP | 2004-275098 | A | 10/2004 |
| JP | 2006-61089 | A | 3/2006 |
| JP | 2006-87328 | A | 4/2006 |
| JP | 2007-6853 | A | 1/2007 |
| JP | 2008-61511 | A | 3/2008 |
| JP | 2008-113565 | A | 5/2008 |
| JP | 2009-254247 | A | 11/2009 |
| JP | 2010-514440 | A | 5/2010 |
| WO | 99/60868 | A1 | 12/1999 |
| WO | 2005/096841 | A1 | 10/2005 |
| WO | WO 2005096841 | A1 * | 10/2005 |

OTHER PUBLICATIONS

Hiroshi Ueno, "Hidden Functions of Glutamate Decarboxylase, Enzyme Involved in Synthesis of GABA; Roles and Applications in Sense of Taste", Dojin News 2010, pp. 1-7, No. 136.
Maria Gomez-Romero et al., "Metabolite profiling and qualification of phenolic compounds in methanol extracts of tomato fruit", Phytochemistry 2010, pp. 1848-1864, vol. 71.
International Searching Authority International Search Report for PCT/JP2012/067781 dated Oct. 2, 2012.
State Intellectual Property Office of the People'S Republic of China, Communication dated Nov. 15, 2014 issued in corresponding Chinese application No. 201280044144.6.
European Patent Office, Communication dated May 15, 2015, issued in counterpart Application No. 12811656.3.

* cited by examiner

*Primary Examiner* — Frederick Krass
*Assistant Examiner* — Michael P Cohen
(74) *Attorney, Agent, or Firm* — Sughrue Mion, PLLC

(57) ABSTRACT

The present invention provides a novel method for improving the flavor of a food, drink, pharmaceutical product, oral care product, or the like. One aspect of the present invention is a method for improving the flavor of a food, drink, pharmaceutical product or oral care product, the method including the step of adding 0.1 to 10000 ppb of γ-aminobutyric acid and 0.01 to 10000 ppb of naringenin to the food, drink, pharmaceutical product, or oral care product.

5 Claims, No Drawings

FLAVOR-IMPROVING METHOD

CROSS REFERENCE TO RELATED APPLICATIONS

This application is a National Stage of International Application No. PCT/JP2012/067781 filed Jul. 12, 2012, claiming priority based on Japanese Patent Application No. 2011-155323 filed Jul. 14, 2011, the contents of all of which are incorporated herein by reference in their entirety.

TECHNICAL FIELD

The present invention relates to a method for improving the flavor of a food, drink, pharmaceutical product, oral care product or the like.

BACKGROUND ART

Due to a trend of health consciousness, there are recently more and more foods and drinks low in sugar or salt, and foods and drinks rich in ingredients which are considered to be beneficial to health. For example, general processes for producing foods and drinks low in sugar or salt include use of high-intensity sweeteners instead of sugar and use of potassium chloride instead of sodium chloride. Many of these alternative ingredients have distinctively unpleasant taste, and substitution or reduction of sugar or salt often makes people unsatisfied with the flavor as compared with that of the original food or drink. Those having sour taste, typified by vinegar, are said to be beneficial to health but many people often do not like eating and drinking them, thus there is a need to improve their flavor.

Patent Literature 1 discloses that hydroxy flavanones reduce the bitter taste of high-intensity sweeteners, minerals, and the like. Patent Literature 2 discloses that γ-aminobutyric acid or salts thereof reduce the unpleasant flavor of high-intensity sweeteners, minerals, and the like.

Although these two literatures disclose improvement of taste by hydroxy flavanones (including naringenin) and γ-aminobutyric acid, the above methods require addition of relatively large amounts of the ingredients but do not always produce sufficient effects.

Patent Literature 3 discloses that combination of high-intensity sweeteners with vegetable juices and alcohol reduces the sweet aftertaste and unpleasant aftertaste of the high-intensity sweeteners. Patent Literature 4 discloses that de-flavored discolored tomato serum is utilized as a salt substitute. Patent Literature 5 discloses that a clear tomato concentrate is used as a taste enhancer.

These three patent literatures disclose that vegetable juices or others considered to contain naringenin and γ-aminobutyric acid are used to improve the flavor of high-intensity sweeteners, foods, or drinks. In the above methods, however, large quantities of vegetable juices and others are required to obtain desired flavor-improving effects, or the properties of the flavor-modifying effects are limited to specific ones such as addition of saltiness. These methods thus cannot be applied to various target products or various types of flavors.

CITATION LIST

Patent Literatures

Patent Literature 1: U.S. Patent Application Publication No. 2002/0188019
Patent Literature 2: International Patent Application Publication No. WO 2005/096841
Patent Literature 3: Japanese Patent Application Laid-Open No. 2009/254247
Patent Literature 4: Japanese Patent Application Laid-Open No. 2010/514440
Patent Literature 5: International Patent Application Publication No. WO 99/60868

SUMMARY OF INVENTION

Technical Problems

It is an object of the present invention to provide a novel method for improving the flavor of a food, drink, pharmaceutical product, oral care product or the like to solve the above-mentioned problems.

Solution to Problems

The present inventors have completed the present invention by finding that a good flavor-improving effect that was not possible before can be obtained by addition of naringenin and γ-aminobutyric acid to foods, drinks, or others under specific conditions.

Specifically, the present invention provides a method for improving the flavor of a food, drink, pharmaceutical product, or oral care product, the method including the step of adding 0.1 to 10000 ppb of γ-aminobutyric acid and 0.01 to 10000 ppb of naringenin to the food, drink, pharmaceutical product, or oral care product.

The present invention also provides a method for improving the flavor of a food, drink, pharmaceutical product, or oral care product, the method including the step of adding γ-aminobutyric acid and naringenin to the food, drink, pharmaceutical product, or oral care product, wherein the improving of the flavor is addition of umami taste, addition of full-bodied flavor, reduction of sourness, reduction of saltiness, or improvement in aftertaste of a mineral.

The present invention further provides a food, drink, pharmaceutical product, or oral care product having flavor improved by the above method for improving the flavor.

Advantageous Effects of Invention

According to the method of the present invention, the use of naringenin and γ-aminobutyric acid in combination can produce various types of flavor-improving effects efficiently on various foods, drinks, or others and the effects can be obtained even with a very small amount of addition, smaller than ever before.

DESCRIPTION OF EMBODIMENTS

In one aspect, a method for improving the flavor of the present invention includes the step of adding γ-aminobutyric acid and naringenin to a food, drink, pharmaceutical product, or oral care product.

In another aspect, a method for improving the flavor of the present invention includes the step of adding 0.1 to 10000 ppb of γ-aminobutyric acid and 0.01 to 10000 ppb of naringenin to a food, drink, pharmaceutical product, or oral care product.

The food, drink, pharmaceutical product, and oral care product targeted for the present invention are not particularly limited as long as they require improvements in flavor in eating/drinking or in use, and include various targets such as liquid, solid, semi-solid, and fluid ones as long as they can obtain benefits from improvement in flavor using γ-aminobutyric acid and naringenin targeted for the present invention.

Foods and drinks include, but are not limited to, liquid products, such as fruit juices, vegetable beverages, carbonated beverages, isotonic drinks, coffee beverages, green tea, tea, yogurt beverages, lactic acid bacteria beverages, energy drinks, soups, noodle soups; solid products, such as candy, gum, gummy candy, jelly, chocolate, ice cream, ham, sausage, and snack; and semi-solid and fluid products, such as curry, stew, hashed beef stew, sauce, dipping sauce, dressing, and whipped cream. Pharmaceutical products are not particularly limited as long as they are made easy to take or swallow by improvement in their flavors. Oral care products include dental powder, toothpaste, liquid toothpaste, and mouthwash.

The types of high-intensity sweeteners are not particularly limited and include, for example, aspartame, sucralose, acesulfame K, saccharin, stevia, neotame, alitame, thaumatin, neohesperidin dihydrochalcone, and glycyrrhiza.

The concentration of γ-aminobutyric acid and naringenin in final products (foods, drinks, pharmaceutical products, oral care products) of which the flavor can be improved can be appropriately set by those skilled in the art according to the properties and required effects of the target final products. The concentration of γ-aminobutyric acid is preferably 0.1 to 10000 ppb, more preferably 1 to 1000 ppb, still more preferably 10 to 100 ppb, and the concentration of naringenin is preferably 0.01 to 10000 ppb, more preferably 0.02 to 1000 ppb, still more preferably 0.05 to 100 ppb.

In addition, the ratio of γ-aminobutyric acid to naringenin is preferably in the range of 1:10000 to 100000:1, more preferably in the range of 1:1000 to 10000:1, still more preferably in the range of 1:100 to 1000:1.

Furthermore, γ-aminobutyric acid and naringenin can be added in any form, for example, as individual compounds or in the form of natural extracts.

In the method for improving the flavor of the present invention, γ-aminobutyric acid and naringenin are preferably added in combination under the above conditions to obtain excellent effects even with very small amounts of addition.

The method for improving the flavor of the present invention exerts various types of flavor-improving effects according to the properties of the target products and others to complement unsatisfied flavor or reduce unpleasant taste. The flavor-improving effects in the present invention are not particularly limited, but include, for example, addition of umami taste, addition of full-bodied flavor, reduction of sourness (reduction of sourness stimulation), reduction of saltiness, sweetness enhancement of high-intensity sweeteners, and improvement of unpleasant aftertaste (sweetness, bitterness, astringency) of high-intensity sweeteners, and flavor improvement of aftertaste (bitterness and astringency) of minerals, such as sodium chloride, magnesium chloride, calcium chloride, potassium chloride, sodium carbonate, magnesium carbonate, calcium carbonate, and potassium carbonate.

More specifically, the method of the present invention can complement thickness-lacking sweetness distinctive of high-intensity sweeteners, and reduce unpleasant bitterness and astringency which remain as aftertaste. In addition, the method of the present invention can complement unsatisfied flavor which is often recognized in low-salt foods and drinks with reduced sodium chloride, and can reduce unpleasant bitterness and astringency which remain as aftertaste and are distinctive of potassium chloride used widely as an alternative ingredient of sodium chloride. The method of the present invention can also harmonize the flavor by reducing sourness stimulation of acids, such as acetic acid, citric acid, lactic acid, and ascorbic acid, and saltiness. The method can also complement less satisfaction from foods and drinks having low content of fruit juice or vegetable juice. The method can add the umami taste and increase the full-bodied flavor to/in curry. In addition to these, the method can exert an effect of increasing the flavor of vegetable beverages, improvement in the flavor of carbonated beverages containing high-intensity sweeteners, improvement in the flavor of isotonic drinks containing high-intensity sweeteners, complexity enhancement of candies, an effect of reducing astringency of tea, and an effect of enhancing the complexity of soups.

As described above, when the method of the present invention is applied to foods, drinks, pharmaceutical products, or oral care products that contain ingredients such as sodium chloride, vinegar, saccharides, and high-intensity sweeteners, the method can reduce astringency, sourness stimulation, or unfavorable flavors, such as bitterness, astringency, sweetness, metallic taste, and chemical taste, distinctive of high-intensity sweeteners, particularly some artificial sweeteners.

Hereinafter, the present invention will be described in more detail by way of Examples, but the present invention is not limited to these Examples.

EXAMPLES

Method for Measuring Amount of Ingredients

1) Naringenin
Analytes were used as they are or were diluted with water to prepare 0.1 to 100 w/v % aqueous solutions and analyzed under the following conditions.
Measurement device: High-performance liquid chromatograph (produced by Agilent Technologies)
Column: Cosmosil 5C18-AR-II, 4.6×150 mm (produced by Nacalai Tesque)
Column temperature: 40° C.
Mobile phase: A; acetonitrile, B; water
A/B=10/90 (0 min)→10/90 (5 min)→30/70 (15 min)→30/70 (30 min)
Flow rate: 0.8 ml/min
Detector: Ultraviolet spectrophotometry (produced by Agilent Technologies)
Detection wavelength: 210 nm 2) γ-Aminobutyric Acid
Analytes were used as they are or were diluted with water to prepare 0.1 to 100 w/v % aqueous solutions and analyzed under the following conditions.
(Analytical method: o-phthalic dialdehyde (OPA) method)
Column: Cadenza CD-C18, 4.6×150 mm (produced by Imtakt Corp.)
Column temperature: 40° C.
Mobile phase: A; 40 mM sodium dihydrogen phosphate (pH 7.8), B; acetonitrile/methanol/water=45/45/10
Gradient: A/B=100/0 (0 min)→100/0 (7 min)→80/20 (18 min)→80/20 (20 min)→55/45 (33.6 min)→0/100 (35 min)→0/100 (45 min)
Flow rate: 1.0 ml/min
Detector: Fluorescence detector (produced by Agilent Technologies)
Detection wavelength: excitation wavelength; 340 nm, fluorescence wavelength; 450 nm (1) Evaluation of Flavor-Improving Effects by Addition of γ-Aminobutyric Acid and Naringenin To a base of a 0.05% aqueous solution of Rebaudio J-100, γ-aminobutyric acid (product name: 4-amino-n-butyric acid, produced by Nacalai Tesque, Inc.) and naringenin (product name: Naringenin, produced by LKT Laboratories, Inc.) were individually added in the amounts as described in the following table, and the flavor-improving effects thereof were evaluated.

Number of evaluators: 3

| Content of GABA (ppb) | Content of naringenin (ppb) | GABA/naringenin | naringenin/GABA | | Evaluation |
|---|---|---|---|---|---|
| \multicolumn{6}{l}{Base: 0.05% aqueous solution of Rebaudio J-100} | | | | | |
| 0.0100 | 10000.0000 | 0.000001 | 1000000.000000 | P | Good fullness of sweetness but lasting unpleasant aftertaste |
| 0.1000 | 10000.0000 | 0.000010 | 100000.000000 | G | Recognition of spreading sweetness and reducing aftertaste |
| 0.1000 | 1000.0000 | 0.000100 | 10000.000000 | G | Recognition of spreading sweetness and reduced aftertaste |
| 1.0000 | 1000.0000 | 0.001000 | 1000.000000 | G | Well-enhanced sweetness |
| 0.1000 | 10.0000 | 0.010000 | 100.000000 | G | Recognition of spreading sweetness |
| 1.0000 | 100.0000 | 0.010000 | 100.000000 | E | Reduced unpleasant aftertaste and enhanced sweetness |
| 1.0000 | 10.0000 | 0.100000 | 10.000000 | E | Spreading sweetness and much more reduced aftertaste than base |
| 10.0000 | 100.0000 | 0.100000 | 10.000000 | E | Feeling of strong sweetness soaking into tongue |
| 10.0000 | 10.0000 | 1.000000 | 1.000000 | E | Spreading sweetness, Juicy |
| 10.0000 | 1.0000 | 10.000000 | 0.100000 | E | Reduced unpleasant astringency, Feeling of strong sweetness |
| 10.0000 | 0.1000 | 100.000000 | 0.010000 | E | Feeling of spreading sweetness |
| 10.0000 | 0.0200 | 500.000000 | 0.002000 | E | Sweetness is spreading on tongue and being milder than base |
| 10.0000 | 0.0100 | 1000.000000 | 0.001000 | E | Reduced aftertaste |
| 100.0000 | 0.0500 | 2000.000000 | 0.000500 | E | Feeling of stronger spread of sweetness and reduced aftertaste |
| 1000.0000 | 0.1000 | 10000.000000 | 0.000100 | G | Better fullness of sweetness in initial taste than that with only γ-aminobutyric acid |
| 1000.0000 | 0.0100 | 100000.000000 | 0.000010 | G | Recognition of spreading sweetness and reduced aftertaste |
| 10000.0000 | 0.0100 | 1000000.000000 | 0.000001 | G | Better fullness of sweetness with almost no aftertaste |
| 100000.0000 | 0.1000 | 1000000.000000 | 0.000001 | P | Better fullness of sweetness but feeling of foreign aftertaste |
| 0.0100 | — | — | — | P | Not different from base |
| 0.1000 | — | — | — | P | Not different from base |
| 1.0000 | — | — | — | P | Reduced total taste |
| 10.0000 | — | — | — | P | Not spreading and weak sweetness |
| 100.0000 | — | — | — | P | Reduced sweetness and watery total taste |
| 500.0000 | — | — | — | P | Weak and flat total taste, Feeling of foreign aftertaste |
| 1000.0000 | — | — | — | VP | Recognition of unpleasant taste that isn't in base |
| 10000.0000 | — | — | — | VP | Recognition of strong unpleasant taste that isn't in base |
| — | 0.0010 | — | — | P | Not different from base |
| — | 0.0100 | — | — | P | Not different from base |
| — | 0.1000 | — | — | P | Persistent unpleasant aftertaste |
| — | 1.0000 | — | — | P | Persistent unpleasant aftertaste |
| — | 10.0000 | — | — | P | No difference in aftertaste from base |
| — | 460.0000 | — | — | P | Bitterness left in mouth |

-continued

| | Base: 0.05% aqueous solution of Rebaudio J-100 | | | |
|---|---|---|---|---|
| Content of GABA (ppb) | Content of naringenin (ppb) | GABA/naringenin | naringenin/GABA | Evaluation |
| — | 1000.0000 | — | — | P Persistent aftertaste in mouth |
| — | 10000.0000 | — | — | P Feeling of strong sweetness and strong unpleasant aftertaste |

VP (very poor): worse than base
P (poor): difference from base not acknowledged, insufficient effects
G (good): different from base, favorable flavor
E (excellent): significantly different from base, very favorable flavor (2) Example of Improved Flavor of High-Intensity Sweetener Mixed were 30 g of a clear tomato concentrate (LycoRed Natural Products Industries Ltd.) and 20 g of 95 vol % ethanol, and stirred for 10 minutes at room temperature. After stirring, the mixture was allowed to stand for 70 hours at room temperature. After allowing the mixture to stand, the upper layer of two separate layers was collected as a flavor-improving material (flavor-improving material 1) (26.6 g). Flavor-improving material 1 contained 4800 ppm of γ-aminobutyric acid and 40 ppm of naringenin. Flavor-improving material 1 was used for the following comparative experiment.
Base: Stevia aqueous solution (0.05% aqueous solution of Rebaudio J-100 produced by Morita Kagaku Kogyo Co., Ltd.)
Analyte: Flavor-improving material 1 (1.5 ppm) was added to the base (Example 1); No additive (only base) (Comparative Example 1)

| | Content of Ingredients in Base (ppb) | | |
|---|---|---|---|
| | γ-Aminobutyric Acid | Naringenin | γ-Aminobutyric Acid:Naringenin |
| Example 1 | 7.2 | 0.06 | 120:1 |
| Comparative Example 1 | 0 | 0 | — |

Number of Evaluators: 9
Results of Sensory Evaluation:
(Number of evaluators who rated each item high)

| | Thickness of Sweetness | Improvement of Unpleasant Bitterness | Improvement of Unpleasant Astringency | Preference |
|---|---|---|---|---|
| Example 1 | 8 | 9 | 9 | 8 |
| Comparative Example 1 | 1 | 0 | 0 | 1 |

(3) Example of Reduced Bitter and Astringent Tastes of Unpleasant Aftertaste of Potassium Chloride
Base: 600 g of soy sauce, 450 g of sugar, 63 g of salt, 300 g of dried bonito extract, and 45 g of potassium chloride were mixed and heated to 90° C. in a water bath to prepare a three times concentrated noodle soup. This noodle soup was diluted with water three times and used as a base for evaluation.
Analyte: To the base, γ-aminobutyric acid and naringenin were added individually in the contents as described in the following table.

| | Content of Ingredients in Base (ppb) | | |
|---|---|---|---|
| | γ-Aminobutyric Acid | Naringenin | γ-Aminobutyric Acid:Naringenin |
| Example 2 | 100 | 100 | 1:1 |
| Comparative Example 2-1 | 0 | 0 | — |
| Comparative Example 2-2 | 0 | 100 | — |
| Comparative Example 2-3 | 100 | 0 | — |

Number of Evaluators: 10
Results of Sensory Evaluation:
(Number of evaluators who rated each item high)

| | Reduction of Bitterness Aftertaste | Reduction of Astringency of Aftertaste | Preference |
|---|---|---|---|
| Example 2 | 10 | 9 | 10 |
| Comparative Example 2-1 | 0 | 0 | 0 |
| Comparative Example 2-2 | 0 | 0 | 1 |
| Comparative Example 2-3 | 3 | 3 | 0 |

(4) Effects of adding Umami Taste and Enhancing Full-Bodied Flavor to/in Curry
Base: 60 g of a commercially available solid curry roux "Vermont Curry <medium hot>" (House Foods Corporation) was added to 500 g of water and dissolved by heating to prepare a curry sauce as a base for evaluation.
Analyte: To the base, γ-aminobutyric acid and naringenin were added individually in the contents as described in the following table.

| | Content of Ingredients in Base (ppb) | | |
|---|---|---|---|
| | γ-Aminobutyric Acid | Naringenin | γ-Aminobutyric Acid:Naringenin |
| Example 3 | 1000 | 10 | 100:1 |
| Comparative Example 3-1 | 0 | 0 | — |

-continued

| | Content of Ingredients in Base (ppb) | | |
|---|---|---|---|
| | γ-Aminobutyric Acid | Naringenin | γ-Aminobutyric Acid:Naringenin |
| Comparative Example 3-2 | 1000 | 0.001 | 1000000:1 |
| Comparative Example 3-3 | 0.02 | 10 | 1:500 |

Number of Evaluators: 11
Results of Sensory Evaluation:
(Number of evaluators who rated each item high)

| | Intensity of Umami Taste | Complexity of Taste | Preference |
|---|---|---|---|
| Example 3 | 10 | 11 | 11 |
| Comparative Example 3-1 | 1 | 0 | 1 |
| Comparative Example 3-2 | 2 | 0 | 1 |
| Comparative Example 3-3 | 1 | 1 | 1 |

(5) Effect of Increasing Flavor of Vegetable Beverage
Base: A commercially available vegetable beverage "Jujitsu Yasai (vegetable glore)" (Ito En, Limited) was used as a base for evaluation.
Analyte: To the base, γ-aminobutyric acid and naringenin were added individually in the contents as described in the following table.

| | Content of Ingredients in Base (ppb) | | γ-Aminobutyric |
|---|---|---|---|
| | γ-Aminobutyric Acid | Naringenin | Acid: Naringenin |
| Example 4 | 10000 | 0.1 | 100000:1 |
| Comparative Example 4-1 | 0 | 0 | — |
| Comparative Example 4-2 | 100000 | 0.1 | 1000000:1 |
| Comparative Example 4-3 | 10000 | 0.01 | 1000000:1 |

Number of Evaluators: 9
Results of Sensory Evaluation:
(Number of evaluators who rated each item high)

| | Complexity of Taste | Reduction of Aftertaste | Preference |
|---|---|---|---|
| Example 4 | 9 | 9 | 9 |
| Comparative Example 4-1 | 0 | 0 | 0 |
| Comparative Example 4-2 | 2 | 3 | 0 |
| Comparative Example 4-3 | 1 | 1 | 1 |

(6) Improvement in Flavor of Carbonated Beverage Containing High-Intensity Sweetener
To 1.2 g of anhydrous citric acid, 0.5 g of sodium citrate, 0.45 g of Rebaudio J-100 (Morita Kagaku Kogyo Co., Ltd.), and 1.0 g of a cider flavor (Takasago International Corporation), water was added to make the total amount of 200 g, and 800 g of carbonated water was further mixed to prepare a base for evaluation.
Analyte: To the base, γ-aminobutyric acid and naringenin were added individually in the contents as described in the following table.

| | Content of Ingredients in Base (ppb) | | γ-Aminobutyric |
|---|---|---|---|
| | γ-Aminobutyric Acid | Naringenin | Acid: Naringenin |
| Example 5 | 5 | 0.05 | 100:1 |
| Comparative Example 5-1 | 5 | 0 | — |
| Comparative Example 5-2 | 0 | 0.05 | — |
| Comparative Example 5-3 | 50000 | 500 | 100:1 |

Number of Evaluators: 12
Results of Sensory Evaluation:
(Number of evaluators who rated each item high)

| | Thickness of Sweetness | Improvement of Unpleasant Bitterness | Improvement of Unpleasant Astringency | Preference |
|---|---|---|---|---|
| Example 5 | 12 | 12 | 11 | 12 |
| Comparative Example 5-1 | 0 | 0 | 2 | 1 |
| Comparative Example 5-2 | 1 | 0 | 0 | 1 |
| Comparative Example 5-3 | 2 | 1 | 0 | 0 |

(7) Improvement in Flavor of Isotonic Drink Containing High-Intensity Sweetener
Mixed were 41 g of a high-fructose corn syrup, 2.1 g of anhydrous citric acid, 1 g of sodium citrate, 0.1 g of vitamin C, 0.6 g of sodium chloride, 0.6 g of potassium chloride, 0.05 g of calcium lactate, 0.05 g of magnesium chloride, and 0.08 g of Sunnett (registered trademark) D (Kirin Kyowa Foods Company, Limited), 0.03 g of sucralose (San-Ei Gen F.F.I., Inc.), and 1.3 g of grapefruit flavor. Water was added thereto to make the total amount of 1000 g, which was used as a base for evaluating isotonic drink containing a high-intensity sweetener.
Analyte: To the base, γ-aminobutyric acid and naringenin were added individually in the contents as described in the following table.

| | Content of Ingredients in Base (ppb) | | γ-Aminobutyric |
|---|---|---|---|
| | γ-Aminobutyric Acid | Naringenin | Acid: Naringenin |
| Example 6 | 10 | 1 | 10:1 |
| Comparative Example 6-1 | 10 | 0 | — |
| Comparative Example 6-2 | 0 | 1 | — |
| Comparative Example 6-3 | 100000 | 100 | 1000:1 |

Number of Evaluators: 20
Results of Sensory Evaluation:
(Number of evaluators who rated each item high)

|  | Thickness of Sweetness | Improvement of Unpleasant Bitterness | Improvement of Unpleasant Astringency | Preference |
|---|---|---|---|---|
| Example 6 | 18 | 19 | 18 | 20 |
| Comparative Example 6-1 | 0 | 1 | 2 | 1 |
| Comparative Example 6-2 | 2 | 0 | 0 | 1 |
| Comparative Example 6-3 | 2 | 1 | 0 | 0 |

(8) Enhancement of Complexity of Candies

Mixed were 300 g of a clear tomato concentrate (LycoRed Natural Products Industries Ltd.) and 30 g of 95 vol % ethanol. This was transferred to a 500 ml flask and heated at 90° C. while stirring. When 30 g of a condensate was obtained by evaporation, the heating was stopped to give 290 g of a residual solution which did not evaporate as flavor-improving material 2. Flavor-improving material 2 contained 9100 ppm of γ-aminobutyric acid and 51 ppm of naringenin. Flavor-improving material 2 was used for the following comparative experiment.

Analyte: (Example 7)

To 400 g of Palatinit (registered trademark) (Mitsui Sugar Co., Ltd.), 142.5 g of a hydrogenated starch hydrolysate and 150 g of water were added and heated for complete dissolution. After heating to 170° C., the resultant was cooled to 150° C. or less, and 0.5 g of Sunnett (registered trademark) D (Kirin Kyowa Foods Company, Limited), 0.25 g of Mirasee (registered trademark) 200 (DSP Gokyo Food & Chemical Co., Ltd.), 1 g of a lemon flavor (Takasago International Corporation), and 0.05 g of flavor-improving material 2 were added, and charged into a mold for molding to prepare 500 g of a candy. This was Example 7-1.

Comparative Example 7-1

To 400 g of Palatinit (registered trademark) (Mitsui Sugar Co., Ltd.), 142.5 g of a hydrogenated starch hydrolysate and 150 g of water were added and heated for complete dissolution. After heating to 170° C., the resultant was cooled to 150° C. or less, and 0.5 g of Sunnett (registered trademark) D (Kirin Kyowa Foods Company, Limited), 0.25 g of Mirasee (registered trademark) 200 (DSP Gokyo Food & Chemical Co., Ltd.), 1 g of a lemon flavor (Takasago International Corporation), and 0.01 g of 1000 times diluted solution of flavor-improving material 2 in water were added, and charged into a mold for molding to prepare 500 g of a candy. This was Comparative Example 7-1.

Comparative Example 7-2

To 400 g of Palatinit (registered trademark) (Mitsui Sugar Co., Ltd.), 142.5 g of a hydrogenated starch hydrolysate and 150 g of water were added and heated for complete dissolution. After heating to 170° C., the resultant was cooled to 150° C. or less, and 0.5 g of Sunnett (registered trademark) D (Kirin Kyowa Foods Company, Limited), 0.25 g of Mirasee (registered trademark) 200 (DSP Gokyo Food & Chemical Co., Ltd.), and 1 g of a lemon flavor (Takasago International Corporation) were added, and charged into a mold for molding to prepare 500 g of a candy. This was Comparative Example 7-2.

|  | Content of Ingredients in Base (ppb) | | γ-Aminobutyric Acid: Naringenin |
|---|---|---|---|
|  | γ-Aminobutyric Acid | Naringenin | |
| Example 7 | 910 | 5.1 | 178:1 |
| Comparative Example 7-1 | 0.182 | 0.001 | 178:1 |
| Comparative Example 7-2 | 0 | 0 | — |

Number of Evaluators: 18
Results of Sensory Evaluation:
(Number of evaluators who rated each item high)

|  | Complexity of Taste | Thickness of Sweetness | Preference |
|---|---|---|---|
| Example 7 | 17 | 18 | 18 |
| Comparative Example 7-1 | 2 | 0 | 1 |
| Comparative Example 7-2 | 1 | 1 | 1 |

(9) Effect of Reducing Astringency of Tea

On 6 g of tea leaves of a commercially available tea "Kokuno aru Koucha (Tea with full-bodied flavors)" (Mitsui Norin Co., Ltd.), 300 g of hot water was poured and allowed to stand for 3 minutes for extraction. After the extraction, the tea leaves were removed through a sieve of 40 meshes and the obtained extract was used as a base.

Analyte: To the base, γ-aminobutyric acid and naringenin were added individually in the contents as described in the following table.

|  | Content of Ingredients in Base (ppb) | | γ-Aminobutyric Acid: Naringenin |
|---|---|---|---|
|  | γ-Aminobutyric Acid | Naringenin | |
| Example 8 | 1 | 100 | 1:100 |
| Comparative Example 8-1 | 1 | 0 | — |
| Comparative Example 8-2 | 0 | 100 | — |
| Comparative Example 8-3 | 0.01 | 100 | 1:10000 |

Number of Evaluators: 9
Results of Sensory Evaluation:
(Number of evaluators who rated each item high)

|  | Reduction of Bitterness of Aftertaste | Reduction of Astringency of Aftertaste | Preference |
|---|---|---|---|
| Example 8 | 9 | 9 | 8 |
| Comparative Example 8-1 | 1 | 2 | 2 |
| Comparative Example 8-2 | 0 | 0 | 2 |
| Comparative Example 8-3 | 0 | 0 | 2 |

(10) Effect of Enhancing Complexity of Soup

To 180 g of hot water, 19.2 g of a commercially available cup soup "Knorr (registered trademark) cup soup potage" (Ajinomoto Co., Inc.) was added and dissolved to make a soup as a base for evaluation.

Analyte: To the base, γ-aminobutyric acid and naringenin were added individually in the contents as described in the following table.

|  | Content of Ingredients in Base (ppb) | | γ-Aminobutyric Acid: Naringenin |
|---|---|---|---|
|  | γ-Aminobutyric Acid | Naringenin |  |
| Example 9 | 10 | 50 | 1:5 |
| Comparative Example 9-1 | 10 | 0 | — |
| Comparative Example 9-2 | 0 | 50 | — |
| Comparative Example 9-3 | 0.05 | 100 | 1:2000 |

Number of Evaluators: 13
Results of Sensory Evaluation:
(Number of evaluators who rated each item high)

|  | Intensity of Umami Taste | Complexity of Taste | Preference |
|---|---|---|---|
| Example 9 | 13 | 12 | 12 |
| Comparative Example 9-1 | 1 | 2 | 1 |
| Comparative Example 9-2 | 0 | 0 | 1 |
| Comparative Example 9-3 | 1 | 2 | 1 |

(11) Effect of Reducing Sour Taste Stimulation

To 200 g of a commercially available beverage "Calpis grape" (Calpis Co., Ltd.), water was added to make up 1000 g, which was used as a base for evaluation.

Analyte: To the base, γ-aminobutyric acid and naringenin were added individually in the contents as described in the following table.

|  | Content of Ingredients in Base (ppb) | | γ-Aminobutyric Acid: Naringenin |
|---|---|---|---|
|  | γ-Aminobutyric Acid | Naringenin |  |
| Example 10 | 0.1 | 0.01 | 10:1 |
| Comparative Example 10-1 | 0.1 | 0 | — |
| Comparative Example 10-2 | 0 | 0.01 | — |
| Comparative Example 10-3 | 0.05 | 0.01 | 5:1 |

Number of Evaluators: 15
Results of Sensory Evaluation:
(Number of evaluators who rated each item high)

|  | Reduction of Sourness Stimulation | Complexity of Taste | Preference |
|---|---|---|---|
| Example 10 | 15 | 14 | 14 |
| Comparative Example 10-1 | 1 | 0 | 1 |
| Comparative Example 10-2 | 0 | 0 | 1 |
| Comparative Example 10-3 | 2 | 2 | 1 |

The invention claimed is:

1. A method for improving flavor of a food, drink, pharmaceutical product, or oral care product, comprising the step of adding 0.1 to 10000 ppb of γ-aminobutyric acid and 0.01 to 10000 ppb of naringenin to the food, drink, pharmaceutical product, or oral care product, wherein the γ-aminobutyric acid and the naringenin are added such that a weight ratio of the γ-aminobutyric acid to the naringenin is from 1:10000 to 100000:1.

2. The method according to claim 1, wherein the improvement of the flavor is addition of umami taste, addition of complexity of taste, reduction of sourness, reduction of saltiness, sweetness enhancement of a high-intensity sweetener, improvement in aftertaste of a high-intensity sweetener, or improvement in aftertaste of a mineral.

3. The method according to claim 1, wherein the γ-aminobutyric acid is added in an amount of 1-1000 ppb and the naringenin is added in an amount of 0.02-1000 ppb.

4. The method according to claim 1, wherein the γ-aminobutyric acid is added in an amount of 10-100 ppb and the naringenin is added in an amount of 0.05-100 ppb.

5. The method according to claim 1, wherein the improvement of the flavor is sweetness enhancement of a high-intensity sweetener and the ratio of γ-aminobutyric acid to the naringenin is 10:1 to 120:1.

* * * * *